United States Patent [19]

Schulte-Elte et al.

[11] 4,277,625

[45] Jul. 7, 1981

[54] PROCESS FOR THE PREPARATION OF MUSCONE

[75] Inventors: Karl-Heinrich Schulte-Elte, Onex; Arnold Hauser, Petit-Lancy; Günther Ohloff, Bernex, all of Switzerland

[73] Assignee: Firmenich SA, Geneva, Switzerland

[21] Appl. No.: 96,054

[22] Filed: Nov. 20, 1979

[30] Foreign Application Priority Data

Dec. 7, 1978 [CH] Switzerland .................. 12510/78

[51] Int. Cl.$^3$ ............................................. C07C 45/60
[52] U.S. Cl. .................................... 568/341; 568/458; 568/459; 568/347; 568/349; 568/598; 568/361; 568/375; 568/828; 260/345.2; 260/338; 260/340.7; 260/340.9 R
[58] Field of Search ............... 568/828, 341, 361, 375, 568/458, 459, 347, 349, 598; 260/345.2, 340.9 R, 338, 340.7

[56] References Cited

U.S. PATENT DOCUMENTS 2,921,940  1/1960  Ramsden ........................ 568/875
3,925,421  12/1975  Story et al. ..................... 568/375

OTHER PUBLICATIONS

Nair et al.; J. Chem. Soc., pp. 4154–4157 (1964).
Nair et al., Tetrahedran, vol. 20, pp. 2601–2607 (1964).
Nair et al., Helv. Chim. Acta., vol. 50, pp. 708–711, 705–707 (1967).
McOmie, Protective Groups in Organic Chemistry, pp. 325–332 (1973).

*Primary Examiner*—Nicky Chan
*Assistant Examiner*—James H. Reamer
*Attorney, Agent, or Firm*—Pennie & Edmonds

[57] ABSTRACT

New process for the preparation of muscone, a valuable macrocyclic musky perfume ingredient. The process makes use of an α,ω-dialdehyde as starting material.

4 Claims, No Drawings

PROCESS FOR THE PREPARATION OF MUSCONE

BRIEF SUMMARY OF THE INVENTION

The invention relates to the field of perfumery, in particular it provides a process for the preparation of muscone (3-methyl-cyclopentadecanone). The new process of the invention makes use of dodeca-4,8-dien-1,12-dial or of dodecan-1,12-dial as starting materials and consists in the following subsequent steps:

a. subjecting to acetalysation a dialdehyde of formula

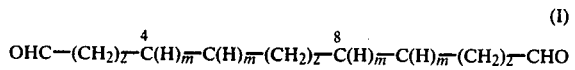

containing two single or two double bonds in positions 4 and 8 of the chain as indicated by the dotted lines and wherein index m stands for 1 or 2, to give a monoacetal of formula

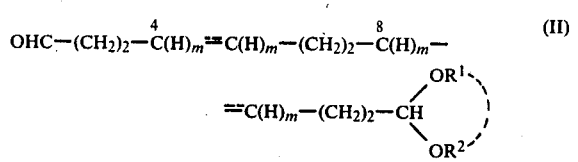

wherein each of symbols $R^1$ and $R^2$ represents, when taken separately, a lower alkyl radical, or when taken together, a lower alkylene radical, b. adding a methallyl-magnesium halide on the obtained mono-acetal to give a hydroxy derivative of formula

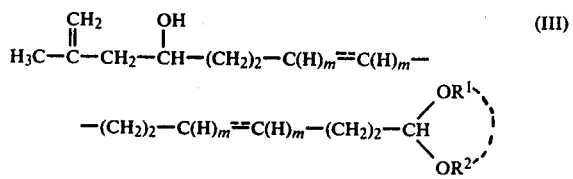

wherein symbols $R^1$ and $R^2$, index m and the dotted lines have the above given meaning, c. cyclising by means of an acidic cyclisation agent compound of formula (III) to yield a bicyclic oxygenated compound of formula

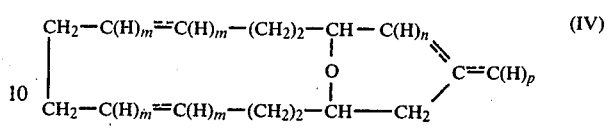

wherein index m and the dotted lines have the above indicated meaning and
(a) n=1 and p=3 or
(b) n=2 and p=2, and d. subjecting said compound (IV) to an isomerisation and a catalytic hydrogenation in an inert organic solvent to yield the desired muscone.

This invention provides also pyranic derivatives of formula

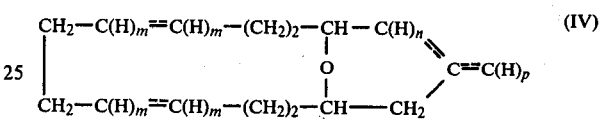

wherein index m, n and p and the dotted lines have the meaning given above.

BACKGROUND OF THE INVENTION

Among the most appreciated musky ingredients known in the art of perfumery, muscone, or 3-methyl-cyclopentadecanone, have acquired a special renown. In spite of this, muscone has not found a widespread utilisation in the art for lack of economical synthetic processes for its preparation.

Among the variety of known processes, one may cite the following:

1.

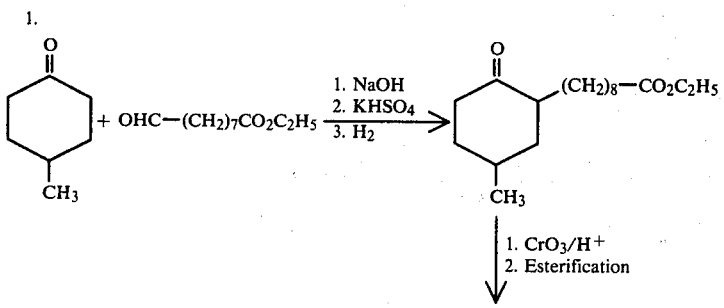

-continued
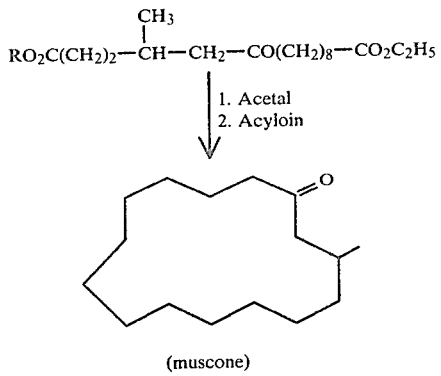
(muscone)
reference: J. Chem. Soc. 4154-7 (1964)
2.
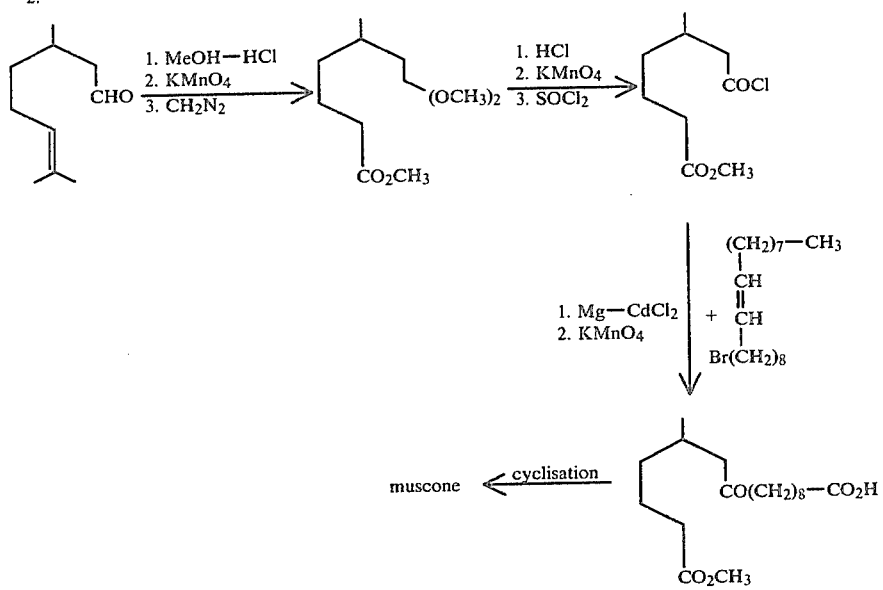
reference: Tetrahedron 20, 11, 2601 (1964)
3.
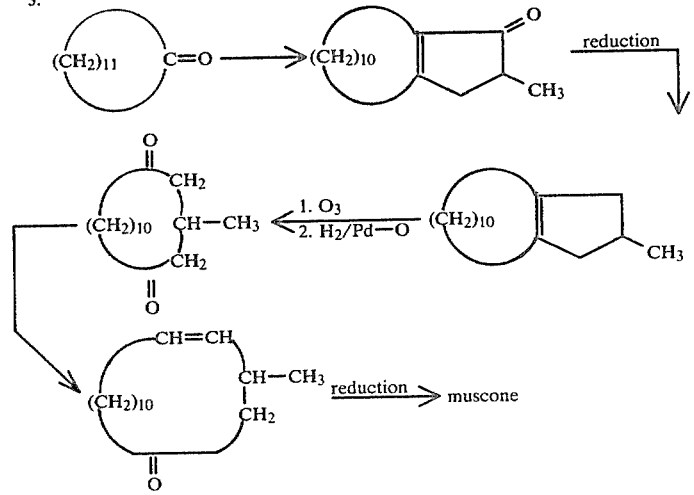
reference: Helv. Chim. Acta. 50, 705, (1967)
or the following variant:
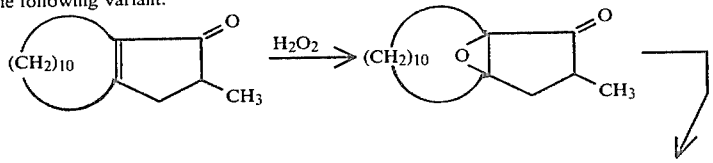

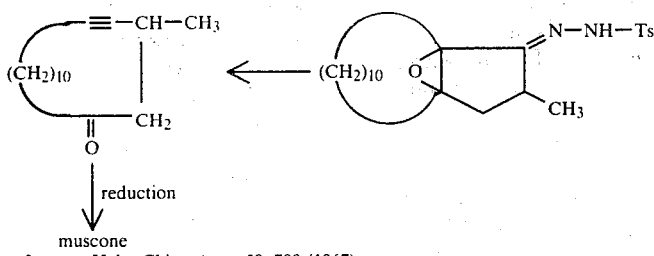

reference: Helv. Chim. Acta, 50, 708 (1967)

By making use of easily available starting materials, the process of the instant invention which is characterized by a limited number of reaction steps represents a new and original solution to the industrial preparation of muscone.

THE INVENTION

The said process can be illustrated by the following reaction scheme:

can be synthesized according to the method described in Compt. Rend. 204, 1948 (1937).

Due to the presence of olefinic double bonds in their molecule, compounds (I) to (IV) can occur under the form of stereoisomers of different configuration, the process of the instant invention can be applied equally satisfactorily to either the pure isomers or any mixture thereof.

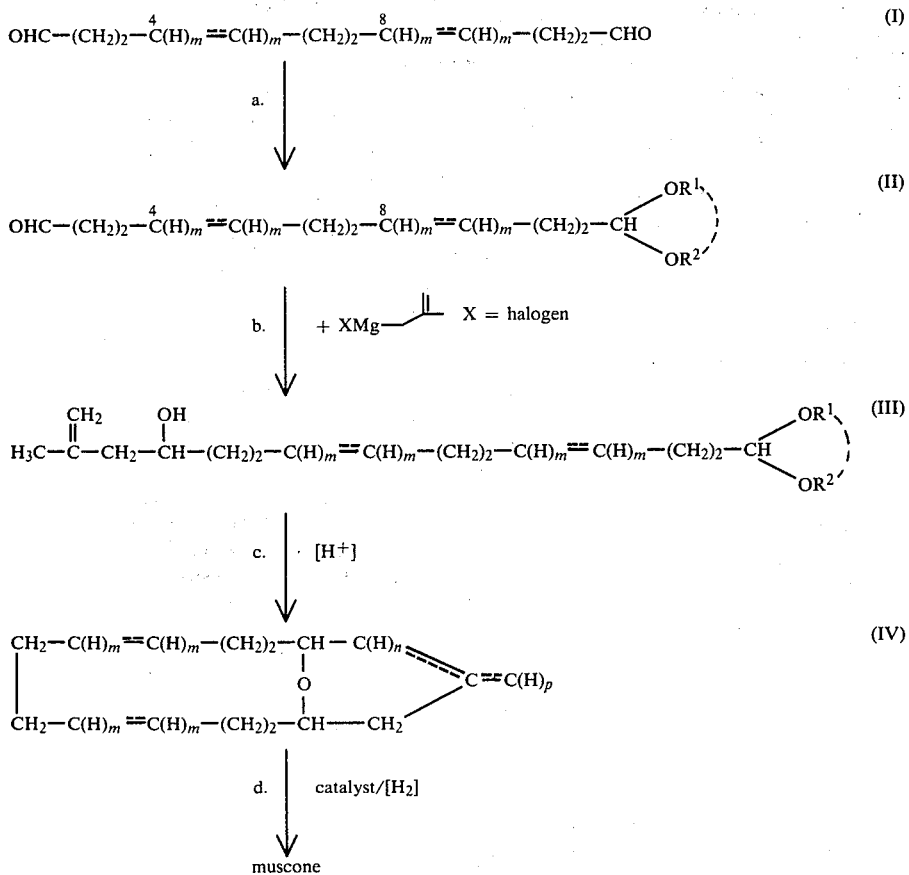

As indicated above, each of symbols $R^1$ and $R^2$ designates either a lower alkyl or alkylene radical. Thus they can represent a methyl, an ethyl or a propyl group, or an ethylene, a propylene or a tetramethylene radical.

Dodeca-4,8-diene-1,12-dial (see formula (I) wherein m=1), used as starting material in the process of the invention, is a readily available starting material which can be otained from cyclododecatriene by means of a selective ozonisation of one of the existing double bonds [see e.g. Swiss Pat. No. 577,445].

Dodecandial [see formula (I) wherein m=2] also used as starting material in the process of the invention

PREFERRED EMBODIMENTS OF THE INVENTION

The first step of the process of the invention, namely the mono-acetalysation of dial (I) can be effected in accordance with known techniques, viz, in the presence of an acid catalyst, for instance in the presence of acid diatomaceous earth. Preferred reactants include ethylene glycol which enables the preparation of ethylene acetal (II) wherein $R^1$ and $R^2$ taken together represent a divalent dimethylenic radical. After separation from the reaction mixture by means of fractional distillation, mono-acetal (II) is treated with a methallyl-magnesium halide and the resulting adduct is hydrolyzed under the conditions of a Grignard reaction, then the thus obtained hydroxy derivative is cyclised by means of an acidic cyclization agent. Suitable acidic agents include protic mineral or organic acids and acidic diatomaceous earth. Such a cyclization is preferably carried out in an inert organic solvent, for instance an aliphatic, cycloaliphatic or aromatic hydrocarbon or an ether. We have observed that good yields of the end product could be obtained by carrying out the cyclization in the presence of p-toluenesulphonic acid in an aromatic hydrocarbon, such as toluene, at a temperature in the vicinity of the boiling temperature of the chosen solvent, e.g. at about 100°–120° C. In order to avoid the formation of by-products, specially originating from condensation reactions, the cyclisation is preferably effected by dissolving at great dilution the starting hydroxy-acetal in the chosen solvent. To this effect, concentrations of about 1 or 2% by weight are utilized.

The last step of the process which consists in the isomerization and catalytic hydrogenation of the pyranic compound of formula (IV), can be carried out in the presence of the usual hydrogenation catalysts, e.g. Raney-nickel or palladium on charcoal.

According to a preferred embodiment, the step of isomerization and hydrogenation is effected in an inert organic solvent, for instance in an aromatic hydrocarbon such as xylene and at a temperature situated in the vicinity of the boiling point thereof.

The invention is better illustrated by the following examples wherein the temperatures are indicated in degrees centigrade.

EXAMPLE 1

Preparation of muscone a. Dodeca-4,8-dien-1,12-dial ethylene-mono-acetal

To a mixture kept at reflux of 970 g (5M) of dodeca-4,8-dien-1,12-dial and 5 g of acidic diatomaceous earth in 5 lt of isopropyl ether in a vessel equipped with a water separator, there were added dropwise, within a period of 10–15 hours, and under vigorous stirring 341 g (5.5M) of ethylene-glycol. Once the addition is over, the reaction mixture was kept refluxing for 3–4 hours and 99 ml of water were isolated. After filtration and evaporation of the volatile fraction there was obtained a residue (1200 g) which was then fractionally distilled to yield 488 g of the desired mono-acetal (purity of about 95%).

IR (film):2700, 1720 cm$^{-1}$;
NMR (CDCl$_3$, 60 MHz): 1.5–2.6 (12H, m); 3.88 (4H, d, j=2.4); 4.84 (1H, t, j=4); 5.2–5.6 (4H, m); 9.77 (1H, s) δ ppm;
MS:M$^+$=238; m/e=220 (2), 195 (15), 175 (8), 163 (2), 141 (13), 119 (14), 99 (30), 73 (100), 55 (16), 41 (42), 29 (13).

b. 2-Methyl-4-hydroxy-pentadeca-1,7,11-trien-15-al ethylene acetal 2 ml of methallyl chloride were added dropwise under vigorous stirring to a suspension of 21.4 g (0.9M) of magnesium turnings in 50 ml of anhydrous diethyl ether and 0.5 ml of ethyl bromide. To this suspension there was then added within about 3 hours a solution of 119 g (0.5M) of the mono-acetal obtained sub letter a. above and 90 g (1.0M) of freshly distilled methallyl chloride in 1 lt of anhydrous ether and 250 ml of tetrahydrofuran. The addition was set at a rate such as to keep the temperature of the reaction mixture below 10°–15°; to this end an external cooling was necessary. The mixture was then kept under stirring at about 15°–20° for 3 hours, whereupon the clear solution obtained on decanting the magnesium in excess was hydrolyzed by means of a saturated aqueous solution of NH$_4$Cl and ice. The aqueous phase was extracted twice with ether and the combined organic extracts were washed with water and an aqueous solution of NaCl until neutrality.

After the usual treatments of drying and evaporation there was obtained a raw material (142 g; yield 96%) which upon bulb distillation (160°–170°/0.1 Torr) gave 125 g of the desired hydroxy-acetal.

IR (film):3345, 3080, 1642, 890 cm$^{-1}$;
NMR (CDCl$_3$, 60 MHz): 1.74 (3H, s); 3.5–4.1 (5H, m); 4.7–5.0 (3H, m); 5.2–5.6 (4H, m) δ ppm;
MS:(M$^+$−57)=237; m/e:222 (1), 208, 195 (9), 177 (3), 159 (4), 147 (7), 141 (13), 129 (12), 119 (13), 109 (18), 99 (40), 93 (39), 79 (49), 73 (100), 67 (36), 55 (39), 43 (96), 31 (83).

c. Bicyclic ether of formula (IV), m=1; n=1; p=3 or n=2; p=2

To a refluxing solution of 500 mg of p-toluene-sulphonic acid in 500 ml of toluene there was added a solution of 14.7 g (0.05M) of the hydroxy-acetal obtained sub letter b. above. The reaction was effected in a vessel equipped with a water separator. Once the addition was over, an additional quantity of 200 mg of p-toluene sulphonic acid was added to the mixture and this was concentrated to roughly one half of its volume by evaporating a part of the toluene present. The concentrated mixture was washed twice with an aqueous solution of NaOH, dried over Na$_2$SO$_4$ and evaporated under reduced pressure.

There was thus obtained 13.3 g of a residue which upon distillation in a bulb apparatus gave at 110°–120°/0.1 Torr 8 g (yield 69%) of bicyclic ether (IV) having a purity of about 95%.

NMR (CDCl$_3$, 90 MHz): 1.66 (3H, d, j=2); 3.2–3.6 (1H,m); 3.7–4.1 (1H, m); 4.15–6.9 (5H, m) δ ppm;
MS: M+=232 (48); m/e: 217 (6), 203 (11), 189 (19), 175 (7), 163 (24), 147 (36), 135 (38), 121 (86), 109 (75), 95 (100), 79 (83), 67 (73), 55 (57), 41 (99).

d. Muscone 2800 mg of palladium on charcoal at 10% in suspension in 50 ml of refluxing xylene were activated during 2 hours by exposing the suspension to a continue flow of hydrogen (flow rate:40 ml/min.).

To this mixture there were then added 6960 mg (0.03M) of the bicyclic ether obtained according to letter c. above and the whole was kept under reflux during 7–8 hours while keeping the flow of hydrogen. The course of the reaction was followed by means of a chromatographic analysis. The excess of hydrogen was eliminated by bubbling through the mixture a flow of nitrogen and the catalyst was recovered by filtration. After concentration of the reaction mixture followed by a fractional distillation with a micro Fisher type apparatus there were obtained 5.0 g (yield 70%) of muscone: B.p. 25°–65°/0.1 Torr.

EXAMPLE 2

By operating in an manner identical to that described above, and using as starting material the ethylene monoacetal of dodecandial instead of the ethylene monoacetal of dodeca-4,8-dien-1,12-dial, we could obtain also muscone but in lower yield.

a. Dodecan-1,12-dial ethylene mono-acetal yield 10–20%
IR:2710, 1725 cm$^{-1}$;
NMR (CDCl$_3$, 60 MHz): 2.1–2.6 (2H, m); 3.6–4.1 (4H, m); 4.83 (1H, t, j=4); 9.75 (1H, t, j=2) δ ppm;
MS:M$^+$=242 (<1); m/e: 113 (<1), 95 (<1), 73 (32), 62 (4), 43 (13), 31 (100).

b. 2-Methyl-4-hydroxy-pentadecan-15-al ethylene monoacetal yield 95%
IR:3500, 3130, 1655, 890 cm$^{-1}$;
NMR (CDCl$_3$, 60 MHz): 1.75–2.3 (6H, m); 2.1 (1H, m); 3.5–4.1 (5H, m); 4.7–5.0 (3H, m) δ ppm;
MS:(M$^+$−85)=213 (<1); 200 (<1), 180 (<1), 163 (1), 144 (2), 124 (10), 109 (7), 89 (28), 81 (6), 73 (22), 63 (13), 56 (100), 43 (70), 31 (56).

c. Bicyclic ether of formula (IV), m=2; n=1; p=3 or n=2; p=2)

yield 15–20%
NMR (CDCl$_3$, 60 MHz): 1.1–2.2 (25H, m); 3.2–3.65 (1H, m); 3.8–4.2 (1H, m); 5.24 (1H, m) δ ppm;
MS:M$^+$=236 (17); m/e: 221 (11), 207 (1), 194 (4), 178 (5), 163 (2), 149 (4), 135 (8), 121 (22), 109 (34), 95 (100), 81 (43), 67 (39), 55 (54), 41 (59), 29 (20).

The said ether could be obtained, in a 95% yield, from the unsaturated bicyclic ether obtained according to Example 1 — see paragraph c., by hydrogenating it in the presence of a Lindler type catalyst.

d. Muscone, prepared by treating the obtained bicyclic ether with hydrogen in the presence of palladium on charcoal, showed analytical characters identical in all respects with those of a pure sample.

What we claim is:

1. Process for the preparation of muscone which comprises a. subjecting to acetalysation in the presence of an acid catalyst a dialdehyde of formula $$\text{OHC}-(\text{CH}_2)_2\overset{4}{=}\text{C(H)}_m\text{=C(H)}_m-(\text{CH}_2)_2\overset{8}{=}\text{C(H)}_m\text{=C(H)}_m-(\text{CH}_2)_2-\text{CHO} \quad (I)$$

containing two single or two double bonds in positions 4 and 8 of the chain as indicated by the dotted lines and wherein index m stands for 1 or 2, to give a monoacetal of formula $$\text{OHC}-(\text{CH}_2)_2\overset{4}{-}\text{C(H)}_m\text{=C(H)}_m-(\text{CH}_2)_2-\overset{8}{\text{C(H)}_m}= \quad (II)$$
$$-\text{C(H)}_m-(\text{CH}_2)_2-\text{CH}\begin{pmatrix}\text{OR}^1\\\text{OR}^2\end{pmatrix}$$

wherein each of symbols R$^1$ and R$^2$ represents, when taken separately, a lower alkyl radical, or when taken together, a lower alkylene radical, b. adding a methallyl-magnesium halide on the obtained mono-acetal and hydrolyzing the resulting adduct under Grignard reaction conditions to give a hydroxy derivative of formula $$\begin{array}{c}\text{CH}_2\quad\quad\text{OH}\\\|\quad\quad\quad|\\\text{H}_3\text{C}-\text{C}-\text{CH}_2-\text{CH}-(\text{CH}_2)_2\text{=C(H)}_m-\text{C(H)}_m-\end{array} \quad (III)$$
$$-(\text{CH}_2)_2-\text{C(H)}_m\text{=C(H)}_m-(\text{CH}_2)_2-\text{CH}\begin{pmatrix}\text{OR}^1\\\text{OR}^2\end{pmatrix}$$

wherein symbols R$^1$ and R$^2$, index m and the dotted lines have the above given meaning, c. cyclising in an inert organic solvent by means of an acidic cyclisation agent compound of formula (III) to yield a bicyclic oxygenated compound of formula $$\begin{array}{c}\text{CH}_2-\text{C(H)}_m\text{=C(H)}_m-(\text{CH}_2)_2-\text{CH}-\text{C(H)}_n\\|\quad\quad\quad\quad\quad\quad\quad\quad\quad\quad\quad\quad\text{O}\quad\quad\diagdown\\\text{CH}_2-\text{C(H)}_m\text{=C(H)}_m-(\text{CH}_2)_2-\text{CH}\text{---}\text{CH}_2\quad\text{C=C(H)}_p\end{array} \quad (IV)$$

wherein index m and the dotted lines have the above indicated meaning and
(a) n=1 and p=3 or
(b) n=2 and p=2, and d. subjecting said compound (IV) to an isomerisation and a catalytic hydrogenation in the presence of a hydrogenation catalyst and in an inert organic solvent to yield muscone.

2. Process according to claim 1 wherein the acetalysation of dialdehyde (I) is effected by means of ethylene glycol.

3. Process according to claim 1 wherein the cyclization of the compound of formula (III) is carried out by means of p-toluene-sulphonic acid in the presence of an inert organic solvent and at a temperature of 100°–120° C.

4. Process according to claim 1 wherein the catalytic hydrogenation is effected in the presence of palladium on charcoal in suspension in an aromatic hydrocarbon and at a temperature located in the vicinity of the boiling point of the chosen solvent.

* * * * *